United States Patent [19]

Nishimura et al.

[11] 4,447,439
[45] May 8, 1984

[54] 2-CYCLIC AMINO-2-(1,2-BENZISOXAZOL-3-YL)ACETIC ACID ESTER DERIVATIVES, PROCESS FOR THE PREPARATION THEREOF AND COMPOSITION CONTAINING THE SAME

[75] Inventors: Haruki Nishimura, Ikeda; Shunsuke Naruto, Ikoma; Hiroyuki Mizuta, Nishinomiya; Toshiaki Kadokawa, Hirakata; Katsuyoshi Kawashima, Kobe, all of Japan

[73] Assignee: Dainaippon Pharmaceutical Co., Ltd., Osaka, Japan

[21] Appl. No.: 411,515

[22] Filed: Aug. 25, 1982

[30] Foreign Application Priority Data

Aug. 26, 1981 [JP] Japan .................. 56-134600

[51] Int. Cl.³ .................... C07D 413/14; A61K 31/42
[52] U.S. Cl. .................... 424/267; 546/187; 546/198; 548/241; 260/244.4
[58] Field of Search .............. 546/187, 198; 260/244.4; 424/256, 267; 548/241

[56] References Cited

U.S. PATENT DOCUMENTS

| | | | |
|---|---|---|---|
| 2,626,260 | 1/1953 | Clinton et al. | 546/198 |
| 4,355,037 | 10/1982 | Strupszewski et al. | 546/198 X |
| 4,390,544 | 6/1983 | Davis et al. | 546/198 X |
| 4,396,770 | 8/1983 | Davis et al. | 546/198 |

OTHER PUBLICATIONS

Reetz, Chem. Abstracts, vol. 53:413a (1959).
Chem. Abstracts, vol. 67:2990e (1967).
Vitali et al., Chem. Abstracts, vol. 72:31781w (1970).
Pigini et al., Chem. Abstracts, vol. 83:193144v (1975).

*Primary Examiner*—Donald G. Daus
*Assistant Examiner*—William A. Teoli, Jr.
*Attorney, Agent, or Firm*—Wegner & Bretschneider

[57] ABSTRACT

Novel 2-cyclic amino-2-(1,2-benzisoxazol-3-yl)acetic acid derivatives of the formula:

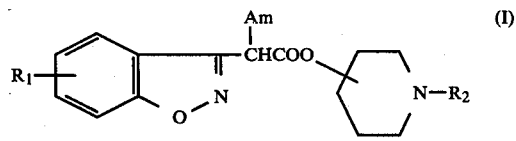

wherein $R_1$ is hydrogen or a halogen atom, $R_2$ is a lower alkyl group, Am is a 5- to 9-membered saturated cyclic amino group which may be substituted by a lower alkyl group, and the group:

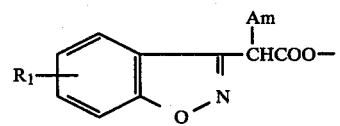

binds to the piperidine moiety at 3- or 4-position of the latter, and their pharmaceutically acceptable acid addition salts and quaternary ammonium salts, process for their preparation, and pharmaceutical compositions containing these compounds. They have potent anticholinergic antispasmodic activity, while they are weak in side effects such as mydriasis, inhibition of salivary secretion and tachycardia.

24 Claims, No Drawings

2-CYCLIC AMINO-2-(1,2-BENZISOXAZOL-3-YL)ACETIC ACID ESTER DERIVATIVES, PROCESS FOR THE PREPARATION THEREOF AND COMPOSITION CONTAINING THE SAME

The present invention relates to novel 1,2-benzisoxazole derivatives having pharmacological activities such as antispasmodic activity. More particularly, it relates to 2-cyclic amino-2-(1,2-benzisoxazol-3-yl)acetic acid ester derivatives and a pharmaceutically acceptable acid addition salt or quaternary ammonium salt thereof, a process for the preparation thereof, and a pharmaceutical composition containing the compound as an active ingredient.

West German Patent No. 859,892 [Chemical Abstracts, 53, 413a (1959)] discloses compounds of the formula:

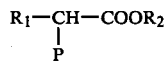

wherein $R_1$ is an aralkyl or aryl residue which may be substituted by one or two alkoxy groups or halogen atoms, $R_2$ is a dialkylaminoalkyl, diarylaminoalkyl or diaralkylaminoalkyl residue, and P is a piperidine residue which combine with the acetic acid residue at the ring nitrogen atom, and its use as a spasmolytica.

Besides, it is disclosed in Chim. Ther., 1966, 408 [Chemical Abstracts, 67, 2990e (1967)] that 1-methyl-3-piperidyl α-piperidinophenylacetate was prepared to test its psychotomimetic properties.

These known compounds are clearly distinguished from the 1,2-benzisoxazole derivatives of the present invention in the chemical structure.

The compounds of the present invention are tertiary amine compounds of the formula:

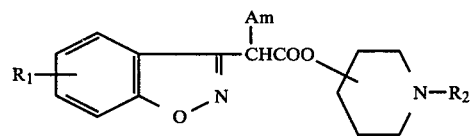

wherein $R_1$ is hydrogen or a halogen atom, $R_2$ is a lower alkyl group, Am is a 5- or 9-membered saturated cyclic amino group which may be substituted by a lower alkyl group, and the group:

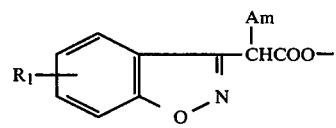

binds to the piperidine moiety at 3- or 4-position of the latter, and a pharmaceutically acceptable acid addition salt or quaternary ammonium salt thereof.

The pharmaceutically acceptable quaternary ammonium salts of the compounds (I) have the following formula:

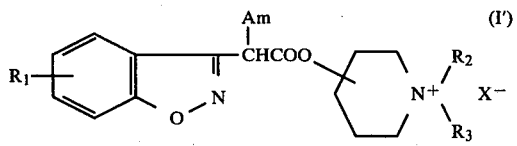

wherein $R_1$, $R_2$, Am and the binding position of the benzisoxazolylacetoxy group are as defined above, $R_3$ is an alkyl group or a phenylalkyl group which may be substituted by a lower alkoxy or methylenedioxy group, and $X^-$ is a pharmaceutically acceptable anion.

The tertiary amine compounds of the formula (I) and an acid addition salt or quaternary ammonium salt thereof have one or more asymmetric carbon atoms and in some cases show geometrical isomerism, and hence, they exist in the form of various stereo-isomers. The present invention includes also these stereo-isomers, their mixture and a racemic mixture.

In the present specification, the term "halogen atom" denotes fluorine, chlorine, bromine and iodine. The term "lower alkyl group" denotes a straight or branched alkyl group having 1 to 3 carbon atoms, such as methyl, ethyl, propyl or isopropyl, preferably methyl or ethyl. The term "lower alkoxy group" denotes a straight or branched alkoxy group having 1 to 3 carbon atoms, such as methoxy, ethoxy, propoxy or isopropoxy, preferably methoxy. The "5- to 9-membered saturated cyclic amino group which may be substituted by a lower alkyl group" represented by Am denotes a 5- to 9-membered saturated cyclic amino group which may be substituted by a straight or branched alkyl group having 1 to 3 carbon atoms at any position and includes 1-pyrrolidinyl, piperidino, methylpiperidino, hexamethyleneimino, heptamethyleneimino, octamethyleneimino, or the like, preferably piperidino, methylpiperidino, hexamethyleneimino or heptamethyleneimino, particularly preferably hexamethyleneimino. The "alkyl group" represented by $R_3$ denotes a straight or branched alkyl group having 1 to 6 carbon atoms, preferably 1 to 4 carbon atoms, more preferably 1 to 2 carbon atoms. The "phenylalkyl group" denotes a straight or branched alkyl group having 1 to 3 carbon atoms which is substituted by phenyl, such as benzyl or phenethyl. The "substituted phenylalkyl group" includes p-methoxybenzyl, 3,4-methylenedioxybenzyl, and 3,4-dimethoxybenzyl. The "anion" represented by $X^-$ denotes an anion formed by removing a proton from a pharmaceutically acceptable and strong inorganic or organic acid and includes a halide ion (e.g. chloride, bromide or iodide ion), a lower alkylsulfate ion (e.g. methylsulfate or ethylsulfate ion), a lower alkylsulfonate ion (e.g. methanesulfonate ion), a substituted or unsubstituted benzenesulfonate ion (e.g. benzenesulfonate or p-toluenesulfonate ion), nitrate ion, preferably bromide or iodide ion, more preferably iodide ion.

Preferred compounds of the present invention are compounds of the formula (I) wherein $R_1$ is hydrogen atom or 5- or 6-halogen atom, $R_2$ is methyl or ethyl group, and Am is a 5- to 8-membered saturated cyclic amino group which may be substituted by methyl group; more preferably $R_1$ is hydrogen atom, $R_2$ is methyl or ethyl group, and Am is hexamethyleneimino group. Specifically preferred compound of the formula (I) is 1-methyl-4-piperidyl 2-hexamethyleneimino-2-(1,2-benzisoxazol-3-yl)acetate.

The quaternary ammonium salts of the formula (I') are especially preferred. Within the quaternary ammonium salts, the ones of the above-mentioned preferred compounds of the formula (I) are still more preferred. Particularly preferred quaternary ammonium salts are the salts of the formula (I') wherein $R_1$ and Am are as defined above as preferred group and both of $R_2$ and $R_3$ are methyl, or either one of $R_2$ and $R_3$ is methyl group and another thereof is ethyl group. Specifically preferred quaternary ammonium salts of the formula (I') are as follows:

1-ethyl-1-methyl-4-[2-hexamethyleneimino-2-(1,2-benzisoxazol-3-yl)acetoxy]piperidinium iodide,
1-ethyl-1-methyl-4-[2-hexamethyleneimino-2-(1,2-benzisoxazol-3-yl)acetoxy]piperidinium bromide,
1,1-dimethyl-4-[2-hexamethyleneimino-2-(1,2-benzisoxazol-3-yl)acetoxy]piperidinium iodide, and
1,1-dimethyl-4-[2-hexamethyleneimino-2-(1,2-benzisoxazol-3-yl)acetoxy]piperidinium bromide, among which the first-mentioned compound is particularly suitable.

The tertiary amine compounds of the formula (I) can be prepared, for example, by reacting a compound of the formula (II):

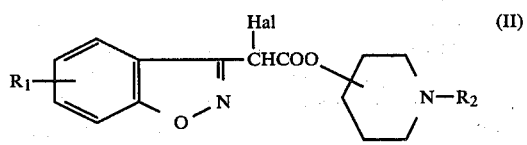

wherein $R_1$ and $R_2$ are as defined above and Hal is a halogen atom such as chlorine, bromine or iodine, or an acid addition salt thereof with a compound of the formula (III):

H—Am          (III)

wherein Am is as defined above.

The reaction of the compound (II) and the compound (III) is usually carried out in an appropriate solvent, such as halogenated hydrocarbons (e.g. dichloromethane, chloroform, dichloroethane), ethers (e.g. diethyl ether, diisopropyl ether, tetrahydrofuran, dioxane), aromatic hydrocarbons (e.g. benzene, toluene, xylene), dialkyl ketones (e.g. acetone, methyl ethyl ketone, methyl isobutyl ketone), esters (e.g. ethyl acetate), acetonitrile, dimethylformamide, or a mixture thereof. The compound (III) is usually used in an amount of equimolar or somewhat excess (e.g. 1.1 to 5 molar ratio) to the compound (II), but may be used in a largely excess amount. The reaction is preferably carried out in the presence of an acid acceptor, such as alkali metal bicarbonates (e.g. sodium bicarbonate, potassium bicarbonate), alkali metal carbonates (e.g. sodium carbonate, potassium carbonate), organic bases (e.g. triethylamine, N-methylmorpholine), or the like. Instead of using a specific acid acceptor, the compound (III) may be used in an excess amount in order to function also as the acid acceptor. The reaction temperature is usually in the range of about 0° to 150° C., preferably about 10° to 70° C., and the reaction period is usually in the range of about 5 minutes to 24 hours. The compound (II) is advantageously used in the form of an acid addition salt thereof.

The compound (I) can be isolated from the reaction mixture and purified by a conventional method. The compound (I) is obtained in the form of a free base or an acid addition salt thereof depending on the kinds of the starting materials and the condition of reaction and subsequent procedures. When the compound (I) is obtained in the form of an acid addition salt, it may be converted into a free base by treating it with a base such as an alkali metal carbonate or ammonia. Besides, when the compound (I) is obtained in the form of a free base, it may be converted into an acid addition salt thereof by treating it with a pharmaceutically acceptable inorganic or organic acid. Suitable examples of the inorganic or organic acid are inorganic acids such as hydrochloric acid, hydrobromic acid, hydroiodic acid, phosphoric acid, nitric acid, sulfuric acid, or the like, and organic acids such as citric acid, oxalic acid, fumaric acid, maleic acid, lactic acid, succinic acid, malic acid, tartaric acid, methanesulfonic acid, or the like.

The compound (I) has one or more asymmetric carbon atoms and hence is usually obtained in the form of a racemic mixture or a mixture of stereo-isomers, but the mixture can be separated into each stereo-isomer by a conventional optical resolution, chromatographic or fractional crystallization method.

The quaternary ammonium salts of the formula (I') can be prepared by reacting a compound of the formula (I) with a compound of the formula (IV):

$R_3$—X          (IV)

wherein $R_3$ is as defined above, and X is a residue of an anion as represented above by $X^-$.

The compound of the formula (IV) includes alkyl halides, dialkyl sulfates, alkyl esters of alkanesulfonic acids, alkyl esters of substituted or unsubstituted benzenesulfonic acids, and substituted or unsubstituted phenylalkyl halides. Suitable examples of the alkyl halides are methyl iodide, methyl bromide, methyl chloride, ethyl iodide, ethyl bromide, ethyl chloride, propyl iodide, propyl bromide, isopropyl iodide, isopropyl bromide, butyl iodide, butyl bromide, isobutyl bromide, or the like. Suitable examples of the dialkyl sulfates are dimethyl sulfate, diethyl sulfate, or the like. Suitable examples of the alkyl esters of alkanesulfonic acids are methyl methanesulfonate, methyl ethanesulfonate, ethyl ethanesulfonate, or the like. Suitable examples of the alkyl esters of substituted or unsubstituted benzenesulfonic acids are methyl p-toluenesulfonate, ethyl p-toluenesulfonate, methyl benzenesulfonate, ethyl benzenesulfonate, or the like. Suitable examples of the substituted or unsubstituted phenylalkyl halides are p-methoxybenzyl bromide, 3,4-methylenedioxybenzyl bromide, 3,4-dimethoxybenzoyl bromide, benzyl bromide, phenethyl bromide, or the like.

The reaction of the compound (I) and the compound (IV) can be carried out by a conventional method which is usually used in the preparation of conventional quaternary ammonium salts, for example, by reacting both compounds in the absence or presence of a solvent. Suitable examples of the solvent are aromatic hydrocarbons (e.g. benzene, toluene, xylene), ethers (e.g. diethyl ether, diisopropyl ether, tetrahydrofuran, dioxane), dialkyl ketones (e.g. acetone, methyl ethyl ketone, methyl isobutyl ketone), lower alcohols (e.g. methanol, ethanol, isopropyl alcohol), acetonitrile, dimethylformamide, or a mixture thereof. The reaction temperature may vary with the kinds of the compound (I), compound (IV) and reaction solvent, but is usually in the range of about 10° to 130° C., and the reaction period is usually in the range of about 10 minutes to 72 hours.

In the above reaction, when the compound (IV) is used in an amount of about equimolar to the compound (I), only the nitrogen atom of the piperidine moiety in the formula (I) is selectively converted into a quaternary form. When a compound of the formula (I) wherein Am is a 7- or more membered cyclic amino group is used, only the nitrogen atom of the piperidine moiety in the formula (I) is in most cases selectively converted into a quaternary form even by using an excess amount of the compound (IV).

When a compound of the formula (I) is reacted with a compound of the formula (IV) wherein $R_3$ is a group different from the group $R_2$, two different quaternary ammonium salts are produced in a ratio of about 1:1 by mole. In the present specification, these two different isomers are defined as follows: the quaternary ammonium salt wherein one of the groups $R_2$ and $R_3$ which has the higher priority determined by the sequence rules of Cahn, Ingold and Prelog [cf. R. S. Cahn et al., Angew. Chem. Intern. Ed. Engl., 5, 385 (1966)] is in the trans-configuration to 2-cyclic amino-2-(1,2-benzisoxazol-3-yl)acetoxy group is defined as α-isomer, and another quaternary ammonium salt is defined as β-isomer. Thus, when $R_2$ and $R_3$ in the formula (I') are methyl and ethyl group, respectively, the quaternary ammonium salt wherein in the $^1$H-NMR spectra the signal of methyl group bonded to the quaternary nitrogen atom appears at the higher field is defined as α-isomer, and the salt wherein the signal appears at the lower field is defined as β-isomer.

The separation of the α-isomer and β-isomer can be carried out by chromatography such as high performance liquid chromatography, or fractional crystallization. When the reaction product produced by the above reaction of a compound (I) and a compound (IV) is recrystallized from an appropriate solvent, it is mostly obtained in the form of a mixed crystal having a molar ratio of the α-isomer to the β-isomer of about 1. Besides, when the kind and amount of the solvent for recrystallization are varied, only either one of the α-isomer and β-isomer may be obtained, or in other cases, the product may be obtained in the form of a mixed crystal wherein the molar ratio of the α-isomer to β-isomer is in the range of about 1/9 to about 9, as is in Example 17 disclosed hereinafter.

The anion ($X^-$) in the compound of the formula (I') may be converted into another anion in a usual manner. For example, a compound of the formula (I') wherein $X^-$ is $X'^-$ is reacted with a compound of the formula (V):

M—X''  (V)

wherein M is an alkali metal atom and X'' is an anionic residue different from X', to convert into a compound of the formula (I') wherein X is $X''^-$. Such a conversion reaction can be carried out in an appropriate solvent, preferably one which can dissolve both of the compound (I') and the compound (V), such as water, lower alcohols (e.g. methanol, ethanol) or a mixture thereof. The reaction temperature is usually in the range of from room temperature to about 100° C., and the reaction period is usually in the range of about 1 to 48 hours. Suitable examples of the compound (V) are sodium iodide, sodium bromide, sodium chloride, sodium nitrate, potassium iodide, potassium bromide, potassium chloride, potassium nitrate, or the like.

The pharmaceutically acceptable acid addition salt or quaternary ammonium salt of the compound (I) may be isolated in the form of a hydrate or a solvate according to conditions used in preparation of the salt.

The starting compounds of the formula (II) are novel compounds and can be prepared, for example, by the process as shown in the following reaction scheme:

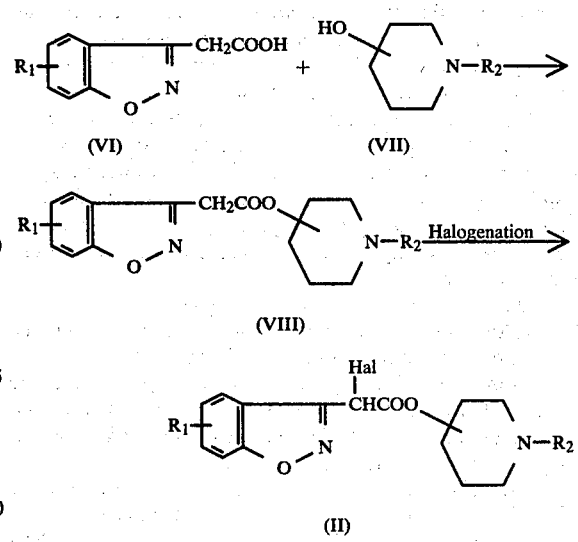

wherein $R_1$, $R_2$ and Hal are as defined above.

The reaction of the compound (VI) and the compound (VII) is carried out under usual conditions for a conventional esterification reaction. The compound (VI) may be used as it is, but may be used in the form of a reactive derivative thereof, such as an acid halide, a mixed anhydride, or a reactive ester. The esterification reaction is carried out in the absence or presence of a solvent and optionally in the presence of an acid (e.g. p-toluenesulfonic acid) or a base (e.g. triethylamine). Suitable examples of the solvent are aromatic hydrocarbons (e.g. benzene, toluene, xylene), ethers (e.g. tetrahydrofuran, dioxane), halogenated hydrocarbons (e.g. dichloromethane, chloroform, dichloroethane), acetonitrile, dimethylformamide, or the like. The reaction temperature may vary according to the kind of the starting compound (VI), i.e. whether the compound (VI) is used as it is or in the form of a reactive derivative thereof, but is usually in the range of about −20° to 150° C., and the reaction period is usually in the range of about 1 to 24 hours.

The compound (VIII) or an acid addition salt thereof is reacted with about equimolar amount of a halogenating agent to give a compound of the formula (II) or an acid addition salt thereof. This halogenation reaction is usually carried out in an appropriate solvent, such as halogenated hydrocarbons (e.g. dichloromethane, chloroform), carbon disulfide, pyridine, dioxane, acetic acid, or a mixture thereof. Suitable examples of the halogenating agent are halogens (e.g. chlorine, bromine), iodine monochloride, N-halogenoamides (e.g. N-bromosuccinimide, N-chlorosuccinimide), sulfuryl halides (e.g. sulfuryl chloride, sulfuryl bromide), halogen complexes (e.g. pyridinium hydrobromide perbromide, dioxane dibromide). The reaction temperature may vary according to the kinds of the halogenating agents or the like, but is usually in the range of about 20° to 130° C., and the reaction period is usually in the range of about 1 to 24 hours. The compound (II) thus obtained may be used in the subsequent step as it is, i.e. in a crude state, or may be used after being purified by recrystallization in the form of an acid addition salt thereof.

The compounds of the formula (I) and pharmaceutically acceptable acid addition salts or quaternary ammonium salts thereof have an excellent anticholinergic antispasmodic activity with less side effects such as mydriasis, inhibition of salivary secretion and tachycardia which are usually observed in conventional anticholinergic agents, and hence, the compounds of the present invention are useful as an antispasmodic.

Pharmacological activities of representative compounds of the present invention were tested, in which atropine sulfate which is a typical anti-cholinergic agent and scopolamine-N-butyl bromide which is a well-known anticholinergic antispasmodic agent were used as reference compounds. The test methods and results are shown below.

Test 1 Antispasmodic activity in vitro (1) Inhibitory effect on contractile response induced by transmural stimulation (Anti-TMS)

From male Hartley strain guinea pig, weighing 300–350 g, section of the ileum about 3 cm in length was prepared and mounted in Tyrode's solution kept at 35° C. and oxygenated with 95% $O_2$—5% $CO_2$, and responses of the ileum were recorded isotonically with an initial tension of 1 g. The ileum was stimulated electrically by the method of W. D. M. Paton [cf. Br. J. Pharmacol., 12, 119 (1957)]. The electrode was made of platinum and the intraluminal electrode was used at a frequency of 5 Hz and at a voltage sufficient to give a maximal response (20–30 V). Test compounds were applied 20 minutes before the stimulation.

(2) Inhibitor effect on contractile response induced by acetylcholine (Anti-ACh)

In the same manner as described in the above experiment (1), ileum preparation was prepared and mounted in Tyrode's solution. The response of the ileum to acetylcholine ($2 \times 10^{-8}$ g/ml) were recorded isotonically. Test compounds were applied 2 minutes before adding the acetylcholine.

In the experiments (1) and (2), each compound was tested in three different concentrations. On the basis of the percent inhibition (mean value of 4 experiments) in each concentration, $IC_{50}$ value, i.e., the concentration required for 50% inhibition of the response induced by transmural electrical stimulation or acetylcholine, was determined by the usual graphic method.

Table 1 shows the results of the experiments (1) and (2).

TABLE 1

| Test compound* | Antispasmodic activity in vitro | | Test Compound* | | |
|---|---|---|---|---|---|
| | $IC_{50}$ (g/ml) | | | $IC_{50}$ (g/ml) | |
| | Anti-TMS | Anti-ACh | | Anti-TMS | Anti-ACh |
| 3 | $1.1 \times 10^{-7}$ | $4.2 \times 10^{-8}$ | 27 | $8.8 \times 10^{-8}$ | $1.4 \times 10^{-8}$ |
| 8 | $1.1 \times 10^{-7}$ | $3.9 \times 10^{-8}$ | 28 | $1.0 \times 10^{-7}$ | $1.3 \times 10^{-8}$ |
| 16 | $3.4 \times 10^{-8}$ | $2.3 \times 10^{-8}$ | 30 | $1.8 \times 10^{-7}$ | $6.4 \times 10^{-8}$ |
| 17(i) | $1.4 \times 10^{-7}$ | $3.6 \times 10^{-8}$ | 31 | $1.2 \times 10^{-7}$ | $5.5 \times 10^{-8}$ |
| 17(ii) | $1.9 \times 10^{-7}$ | $3.6 \times 10^{-8}$ | 33 | $1.8 \times 10^{-7}$ | $3.2 \times 10^{-8}$ |
| 17(iii) | $2.0 \times 10^{-7}$ | $9.9 \times 10^{-8}$ | 34 | $4.4 \times 10^{-8}$ | $3.3 \times 10^{-8}$ |
| 20 | $1.2 \times 10^{-7}$ | $2.0 \times 10^{-8}$ | 36 | $1.1 \times 10^{-7}$ | $2.9 \times 10^{-8}$ |
| 21 | $9.0 \times 10^{-8}$ | $3.2 \times 10^{-8}$ | 37 | $2.4 \times 10^{-7}$ | $7.2 \times 10^{-8}$ |
| 22 | $9.6 \times 10^{-8}$ | $2.2 \times 10^{-8}$ | 38 | $2.7 \times 10^{-8}$ | $2.4 \times 10^{-8}$ |
| 23 | $7.4 \times 10^{-8}$ | $3.6 \times 10^{-8}$ | 39 | $5.8 \times 10^{-8}$ | $5.1 \times 10^{-8}$ |
| 24 | $1.0 \times 10^{-7}$ | $3.6 \times 10^{-8}$ | 42 | $3.4 \times 10^{-7}$ | $7.8 \times 10^{-8}$ |
| 26 | $8.8 \times 10^{-8}$ | $3.9 \times 10^{-8}$ | 44 | $2.9 \times 10^{-7}$ | $8.0 \times 10^{-8}$ |
| Atropine sulfate | $3.5 \times 10^{-8}$ | $5.0 \times 10^{-9}$ | Scopolamine-N—butyl bromide | $4.4 \times 10^{-7}$ | $8.9 \times 10^{-8}$ |

[Note]
*The figure means the number of working examples disclosed hereinafter for preparing the test compound.

As shown in Table 1, the compounds of the present invention have potent antispasmodic activities. Their activities are stronger than or nearly equal to those of scopolamine-N-butyl bromide, while somewhat weaker than those of atropine sulfate.

Test 2 Antispasmodic activity in vivo (1) Inhibitor effect on contractile response induced by carbachol (Anti-Car)

This effect was examined using the strain gauge force transducer as described by X. B. Pascaud et al. [cf. Am. J. Physiol., 235, E532 (1978)]. The transducer was sutured on the serosa of the stomach in anesthetized male Wistar strain rats, weighing about 250 g. This transducer can record simultaneously contractions and tone variation of the muscle. The contractile response induced by carbachol (10 μg/kg, i.v.) was estimated before and after administration of test compound. Inhibitory effect of test compound was expressed as a percent inhibition of the response. $ID_{50}$ value, i.e., the dose required for 50% inhibition of the response induced by carbachol, was determined from regression line calculated by the maximum percent inhibition at each dose level.

(2) Inhibitory effect on spontaneous gastric motility (Anti-SGM)

This effect was examined using male Wistar strain rats, weighing about 250 g, with chronically implanted strain gauge force transducer as mentioned in the experiment (1). The rats were usually allowed to stand for 3–5 days for recovery from the surgery and fasted for 18 hours before experiment. Then, spontaneous gastric motility in conscious rats were recorded and the sum of amplitude of each contraction was calculated every 15 minutes. Inhibitory effect of test compound by oral administration was expressed as a percent inhibition of initial spontaneous motility. $ID_{50}$ value, i.e., the dose required for 50% inhibition of spontaneous motility, was determined from regression line calculated by the maximum percent inhibition at each dose level.

Table 2 shows the results of the experiments (1) and (2).

TABLE 2

| Test compound | Antispasmodic activity in vivo | |
|---|---|---|
| | $ID_{50}$ (μg/kg, i.v.) Anti-Car | $ID_{50}$ (mg/kg, p.o.) Anti-SGM |
| 17(i)* | 18.7 | 26.3 |
| Atropine sulfate | 8.4 | 1.7 |
| Scopolamine-N—butyl bromide | 20.1 | 100 |

[Note]
*The figure means the compound obtained in Example 17(i).

It is evident from Table 2 that the anti-spasmodic activities in vivo of the compound of the present invention are more potent than those of scopolamine-N-butyl bromide.

Test 3 Mydriatic activity

This activity was examined according to the method of P. Pelewka [cf. Arch. Exp. Path. Pharmakol., 168, 307 (1932)], using male Wistar strain rats, weighing 150–220 g. Mydriasis caused by oral administration of test compound was microscopically observed at a distance of 30 cm from the source of constant light (30 W-fluorescent light) in the rats. $ED_{50}$ value, i.e., 50% of the dose at which test compound dilates the pupil size 3 mm in a diameter, was determined by the usual graphic method.

Table 3 shows the result of the Test 3 and the safety index of test compounds calculated on the basis of the results of the Test 2 (2) and Test 3.

TABLE 3

| Test compound | Mydriatic activity and safety index | |
|---|---|---|
| | Mydriatic activity $ED_{50}$ (mg/kg, p.o.) | Safety index* |
| 17(i)** | >3000 | >114 |
| Atropine sulfate | 3.5 | 2 |
| Scopolamine-N—butyl bromide | 227 | 2 |

[Note]
*This index is determined by dividing $ED_{50}$ of mydriatic activity by $ID_{50}$ of Anti-SGM.
**The figure means the compound obtained in Example 17(i).

As shown in Table 3, the mydriatic activity of the compound of the present invention is far weaker than those of atropine sulfate and scopolamine-N-butyl bromide. The compound of the present invention has much higher safety index than the two reference compounds. It is suggested that the compound of the present invention has a wide separability of therapeutic effects from unfavorable side effect.

Test 4 Acute lethal toxicity

The mortality was observed for 7 days after single oral administration of the compound obtained in Example 17 (i) to male and female Jcl:SD strain rats. The $LD_{50}$ value of the compound was 5430 mg/kg in male rats and 6320 mg/kg in female rats.

The compounds of the formula (I) and pharmaceutically acceptable acid addition salts or quarternary ammonium salts thereof are useful as an antispasmodic for the treatment of peptic ulcer and various hyperactive symptoms in gastrointestinal tract, for example, spastic constipation, irritable diarrhea, cardiospasm and pylorospasm in mammals including human being.

The compounds (I) and pharmaceutically acceptable acid addition salts or quarternary ammonium salts thereof can be administered by oral, parenteral or intrarectal route, preferably by oral route. The clinical dose of the compound (I) and pharmaceutically acceptable acid addition salts or quaternary ammonium salts thereof may vary according to the kinds of the compound, administration routes, severity of disease, age of patients, or the like, but is usually in the range of 0.05 to 40 mg per kg of body weight per day, preferably 0.1 to 20 mg per kg of body weight per day, in human. The dose may be divided and administered in two to several times per day.

The compounds (I) and pharmaceutically acceptable acid addition salts or quarternary ammonium salts thereof are usually administered to patients in the form of a pharmaceutical composition which contains a non-toxic and effective amount of the compounds. The pharmaceutical composition is usually prepared by admixing the active compounds (I) or their salts with conventional pharmaceutical carrier materials which are unreactive with the active compounds (I) or their salts. Suitable examples of the carrier materials are lactose, glucose, mannitol, dextran, cyclodextrin, starch, sucrose, magnesium aluminosilicate tetrahydrate, synthetic aluminum silicate, microcrystalline cellulose, sodium carboxymethylcellulose, hydroxypropylstarch, calcium carboxymethylcellulose, ion exchange resin, methylcellulose, gelatin, acacia, hydroxypropylcellulose, low substituted hydroxypropylcellulose, hydroxypropyl methylcellulose, polyvinylpyrrolidone, polyvinyl alcohol, light anhydrous silicic acid, magnesium stearate, talc, tragacanth, bentonite, veegum, carboxyvinyl polymer, titanium dioxide, sorbitan fatty acid ester, sodium lauryl sulfate, cacao butter, glycerin, glycerides of saturated fatty acids, anhydrous lanolin, glycerogelatin, polysorbate, macrogol, vegetable oils, wax, propylene glycol, water, or the like.

The pharmaceutical composition may be in the dosage form of tablets, capsules, granules, fine granules, powders, syrups, suspension, suppositories, injections, or the like. These preparations may be prepared by conventional methods. Liquid preparations may be prepared by dissolving or suspending the active compounds in water or other suitable vehicles, when used. Tablets may be coated in a conventional manner.

The pharmaceutical composition may contain as the active ingredient the compound (I) or its pharmaceutically acceptable acid addition salt or quaternary ammonium salt in the ratio of 0.5% by weight or more, preferably 1 to 70% by weight, based upon the whole weight of the compositions. The composition may further contain one or more other therapeutically active compounds.

The present invention is illustrated more specifically by the following Examples and Reference Examples. It should be understood that the invention is not limited to these examples. The compounds were identified by elemental analysis, mass spectrum, infrared spectrum, nuclear magnetic resonance (NMR) spectrum, etc.

EXAMPLE 1

1-Methyl-4-piperidyl 2-heptamethyleneimino-2-(1,2-benzisoxazol-3-yl)acetate oxalate A solution of bromine (1.48 g) in glacial acetic acid (3 ml) was added dropwise with stirring to a solution of 1-methyl-4-piperidyl 1,2-benzisoxazole-3-acetate hydrobromide (3.0 g) in glacial acetic acid (6 ml). After the reaction mixture was stirred for 40 minutes at 60° C., it was diluted with water (100 ml) and extracted with two 100-ml portions of chloroform. The chloroform solution was dried over anhydrous sodium sulfate and evaporated to give crude 1-methyl-4-piperidyl 2-bromo-2-(1,2-benzisoxazol-3-yl)acetate hydrobromide (3.2 g). The hydrobromide thus obtained was dissolved in chloroform (15 ml) and thereto was added heptamethyleneimine (4.5 ml). The resulting mixture was stirred overnight at room temperature and evaporated in vacuo to give a residue, to which water (50 ml) was added. The resulting mixture was extracted with two 100-ml portions of toluene. The toluene layer was extracted with 5% hydrochloric acid (70 ml). The aqueous layer was made alkaline with aqueous ammonia solution and extracted with toluene. The toluene layer was dried over anhydrous sodium sulfate and evaporated in vacuo to give an oily residue (2.25 g). The residue and oxalic acid (0.74 g) were dissolved in ethanol (10 ml). The solution was concentrated in vacuo to about a half volume. To the residue was added diethyl ether until it became turbid. The crystals precipitated were collected by filtration and recrystallized from ethanol-diethyl ether to give 1-methyl-4-piperidyl 2-heptamethyleneimino-2-(1,2-benzisoxazol-3-yl)acetate oxalate (2.41 g), m.p. 170°–173° C.

EXAMPLES 2 TO 15

Various compounds of the formula:

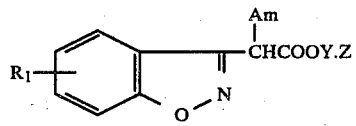

as listed in the following Table 4 were prepared in substantially the same manner as in Example 1, using the corresponding 1,2-benzisoxazole-3-acetic acid esters and amines.

TABLE 4

| Ex. | $R_1$ | Am | Y | Z | m.p. (°C.) (Recry. Solv.*) |
|---|---|---|---|---|---|
| 2 | H | piperidin-1-yl | 1-methylpiperidin-4-yl | 2HBr | 225–230 (AC) |
| 3 | H | hexamethyleneimin-1-yl | 1-ethylpiperidin-4-yl | — | 114–116 (E) |
| 4 | H | hexamethyleneimin-1-yl | 1-ethylpiperidin-4-yl | — | Oil |
| 5 | H | hexamethyleneimin-1-yl | 1-ethylpiperidin-4-yl | 2HBr | 214–216 (AC) |
| 6 | H | 2-methylpiperidin-1-yl | 1-methylpiperidin-4-yl | 2(CO$_2$H)$_2$ | 180–182 (AC—H) |
| 7 | H | 4-methylpiperidin-1-yl | 1-ethylpiperidin-4-yl | 2HBr | 222–224 (AC—M) |
| 8 | H | hexamethyleneimin-1-yl | 1-methylpiperidin-4-yl | — | 125–127 (AC—E) |
| 9 | H | 2-methylpiperidin-1-yl | 1-methylpiperidin-4-yl | 2HBr | 199–201 (AC—M) |
| 10 | H | pyrrolidin-1-yl | 1-methylpiperidin-4-yl | 2HBr | 206–211 (AC—M) |

TABLE 4-continued

| Ex. | R₁ | Am | Y | Z | m.p. (°C.) (Recry. Solv.*) |
|---|---|---|---|---|---|
| 11 | H | −N⟨ ⟩ (pyrrolidinyl) | −⟨ ⟩NCH₃ | 2HBr | 219–222 (A—E) |
| 12 | H | −N⟨ ⟩−CH₃ | −⟨ ⟩NCH₃ | 2(CO₂H)₂ | 80–85 (AC—E) |
| 13 | 5-Cl | −N⟨ ⟩ (hexamethyleneimino) | −⟨ ⟩NCH₃ | — | Oil |
| 14 | 6-F | −N⟨ ⟩ (hexamethyleneimino) | −⟨ ⟩NCH₃ | — | Oil |
| 15 | 5-F | −N⟨ ⟩ (hexamethyleneimino) | −⟨ ⟩NCH₃ | — | Oil |

[Note]
*The abbreviations are as follows:
A: ethanol, AC: acetone, E: diethyl ether, H: hexane, M: methanol.

EXAMPLE 16

1-Methyl-4-piperidyl 2-hexamethyleneimino-2-(1,2-benzisoxazole-3-yl)acetate

Hexamethyleneimine (52 g) was added dropwise at room temperature with stirring to a suspension of 1-methyl-4-piperidyl 2-bromo-2-(1,2-benzisoxazol-3-yl)acetate hydrobromide (46 g) in chloroform (200 ml). After stirring for 20 hours at room temperature, the reaction mixture was evaporated in vacuo to give a residue. 5% Sodium carbonate (100 ml) was added to the residue, and the mixture was extracted with chloroform. The chloroform layer was washed with water, dried over anhydrous sodium sulfate, and evaporated in vacuo. The residue was recrystallized from diethyl ether-hexane to give 1-methyl-4-piperidyl 2-hexamethyleneimino-2-(1,2-benzisoxazol-3-yl)acetate (28 g), m.p. 78°–80° C.

EXAMPLE 17

1-Ethyl-1-methyl-4-[2-hexamethyleneimino-2-(1,2-benzisoxazol-3-yl)acetoxy]piperidinium iodide (i) Ethyl iodide (2.1 g) was added to a solution of 1-methyl-4-piperidyl 2-hexamethyleneimino-2-(1,2-benzisoxazol-3-yl)acetate (1.0 g) in acetone (8 ml). The mixture was refluxed for 1 hour and evaporated in vacuo. The residue was recrystallized from isopopyl alcohol (25 ml) to give 1-ethyl-1-methyl-4-[2-hexamethyleneimino-2-(1,2-benzisoxazol-3-yl)acetoxy]piperidinium iodide (1.3 g), m.p. 158°–159° C. ¹H-NMR (CDCl₃)δ: 3.30 (s), 3.45 (s) (N—CH₃, the ratio of the area of the former peak to that of the latter one was about 1)

The ¹H-NMR spectral data described above indicated that the product was obtained as mixed crystals of the α/β ratio of 1. The result of the elemental analyses suggested that the product was in the form of hemihydrate.

(ii) The product (8 g) obtained in the above Example (i) was recrystallized three times from a mixture of chloroform, ethyl acetate and diisopropyl ether (4:1:1) to give 1-ethyl-1-methyl-4-[2-hexamethyleneimino-2-(1,2-benzisoxazol-3-yl)acetoxy]piperidinium iodide (0.35 g), m.p. 148° C., in which the α/β ratio was about 9.

(iii) Ethyl p-toluenesulfonate (5.3 g) was added to a solution of 1-methyl-4-piperidyl 2-hexamethyleneimino-2-(1,2-benzisoxazol-3-yl)acetate (2.0 g) in acetonitrile (30 ml). The mixture was refluxed for 16 hours and evaporated. The residue was washed with diethyl ether (50 ml) and then recrystallized from a mixture of acetone, ethyl acetate and diethyl ether (3:3:1). There was obtained 1-ethyl-1-methyl-4-[2-hexamethyleneimino-2-(1,2-benzisoxazol-3-yl)acetoxy]piperidinium p-toluenesulfonate (2.07 g), m.p. 132°–140° C., in which the α/β ratio was about 1.

The product thus obtained was recrystallized from a mixture of acetone, ethyl acetate and diethyl ether (4:5:5) to give the product (0.8 g), m.p. 138°–140° C., in which the α/β ratio was about ¼. This product (0.5 g) was dissolved in methanol (30 ml) and thereto was added a solution of potassium iodide (2.6 g) in water (50 ml). The methanol was distilled off from the mixture and the residue was extracted with chloroform. The chloroform layer was evaporated. The residue was recrystallized from a mixture of acetone, ethyl acetate and diethyl ether (1:1:4) to give 1-ethyl-1-methyl-4-[2-hexamethyleneimino-2-(1,2-benzisoxazol-3-yl)acetoxy]piperidinium iodide (0.30 g), m.p. 170°–174° C., in which the α/β ratio was about 1/9.

(iv) A mixture of 1-methyl-4-piperidyl-2-hexamethyleneimino-2-(1,2-benzisoxazol-3-yl)acetate (60 g), ethyl iodide (126 g), and acetone (500 ml) was stirred at room temperature for 17 hours. The resulting crystals were collected by filtration to give 1-ethyl-1-methyl-4-[2-hexamethyleneimino-2-(1,2-benzisoxazol-3-yl)acetoxy]piperidinium iodide (58 g), in which the α/β ratio was about 1. Diethyl ether (500 ml) was added to the mother liquor. The mixture was allowed to stand at 0° C. to give additional crystals (24 g), which were recrystallized repeatedly from acetone. There was obtained the α-isomer (4.8 g), m.p. 177°–179° C.

EXAMPLE 18

1-Benzyl-1-methyl-4-[2-hexamethyleneimino-2-(1,2-benzisoxazol-3-yl)acetoxy]piperidinium bromide Benzyl bromide (3.2 ml) was added to a solution of 1-methyl-4-piperidyl 2-hexamethyleneimino-2-(1,2-benzisoxazol-3-yl)acetate (1.0 g) in toluene (5 ml). The mixture was heated at 100° C. for 40 minutes and allowed to cool, and thereto was added diethyl ether. The crystals precipitated were collected by filtration and recrystallized from a mixture of ethanol and diethyl ether. There was obtained 1-benzyl-1-methyl-4-[2-hexamethyleneimino-2-(1,2-benzisoxazol-3-yl)acetoxy]-piperidinium bromide (0.58 g), m.p. 190°–192° C., in which the α/β ratio was about 3/2.

EXAMPLE 19

1-Methyl-1-(3,4-methylenedioxybenzyl)-4-[2-hexamethyleneimino-2-(1,2-benzisoxazol-3-yl)acetoxy]-piperidinium bromide 1-Methyl-4-piperidyl 2-hexamethyleneimino-2-(1,2-benzisoxazol-3-yl)acetate was reacted with 3,4-methylenedioxybenzyl bromide in substantially the same manner as in Example 18. To the reaction mixture was added diethyl ether. The crystals precipitated were collected by filtration and recrystallized from a mixture of acetone, ethanol and diethyl ether. There was obtained 1-methyl-1-(3,4-methylenedioxybenzyl)-4-[2-hexamethyleneimino-2-(1,2-benzisoxazol-3-yl)acetoxy]-piperidinium bromide, m.p. 180°–190° C., in which the α/β ratio was about 3/7.

EXAMPLE 20

1,1-Dimethyl-4-[2-hexamethyleneimino-2-(1,2-benzisoxazol-3-yl)acetoxy]piperidinium iodide A mixture of 1-methyl-4-piperidyl 2-hexamethyleneimino-2-(1,2-benzisoxazol-3-yl)acetate (3.3 g), methyl iodide (8 g), and toluene (23 ml) was stirred at room temperature for 20 hours and then evaporated. The residue was recrystallized from ethanol to give 1,1-dimethyl-4-[2-hexamethyleneimino-2-(1,2-benzisoxazol-3-yl)acetoxy]piperidinium iodide (4.1 g), m.p. 210°–211° C.

EXAMPLE 21

1,1-Dimethyl-4-[2-piperidino-2-(1,2-benzisoxazol-3-yl)acetoxy]piperidinium iodide A mixture of 1-methyl-4-piperidyl 2-piperidino-2-(1,2-benzisoxazol-3-yl)acetate (1 g), methyl iodide (2.5 g), and acetone (10 ml) was allowed to stand at room temperature for 5 hours. The resulting crystals were recrystallized from ethanol-methanol to give 1,1-dimethyl-4-[2-piperidino-2-(1,2-benzisoxazol-3-yl)acetoxy]piperidinium iodide (1.1 g), m.p. 176°–178° C.

EXAMPLES 22 TO 44

Various compounds of the formula:

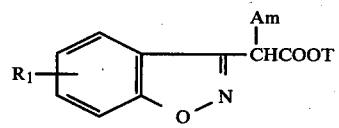

as listed in the following Table 5 were prepared in substantially the same manner as in Examples 20 and 21, using the corresponding 2-cyclic amino-2-(1,2-benzisoxazol-3-yl)acetic acid esters and the compound of formula: $R_6X$ as listed in the following Table 5. When the two groups bonded to the quaternary nitrogen atom of the product are different, the products in which the α/β ratio is about 1 are obtained in all the cases.

TABLE 5

| Ex. | $R_6X$ | $R_1$ | Am | T | m.p. (°C.) (Recry. Solv.*) |
|---|---|---|---|---|---|
| 22 | $CH_3I$ | H | —N(7-membered ring) | piperidinium $N^+$, $CH_3$, $C_2H_5$  I$^-$ | 188–189 (A) |
| 23 | $CH_3I$ | H | —N(6-membered ring with CH$_3$) | piperidinium $N^+$, $CH_3$, $CH_3$  I$^-$ | 211–214 (M) |
| 24 | $CH_3I$ | H | —N(7-membered ring) | piperidinium $N^+$, $CH_3$, $CH_3$  I$^-$ | 208–209 (M) |
| 25 | n-$C_3H_7$Br | H | —N(7-membered ring) | piperidinium $N^+$, $CH_3$, $C_3H_7$  Br$^-$ | 181–183 (A—E) |

TABLE 5-continued

| Ex. | R₆X | R₁ | Am | T | | m.p. (°C.) (Recry. Solv.*) |
|---|---|---|---|---|---|---|
| 26 | CH₃I | H | piperidine | N⁺(CH₃)₂ | I⁻ | 170–171 (EA) |
| 27 | CH₃I | H | azocane (8-membered) | N⁺(CH₃)₂ | I⁻ | 195–196 (A—E) |
| 28 | (CH₃)₂SO₄ | H | azocane | N⁺(CH₃)₂ | CH₃SO₄⁻ | 153–154 (A—E) |
| 29 | n-C₄H₉Br | H | azocane | N⁺(CH₃)(C₄H₉) | Br⁻ | 173–178 (A—E) |
| 30 | (C₂H₅)₂SO₄ | H | azocane | N⁺(CH₃)(C₂H₅) | C₂H₅SO₄⁻ | 123–125 (A—E) |
| 31 | C₂H₅Br | H | azocane | N⁺(CH₃)(C₂H₅) | Br⁻ | 177–178 (AC—E) |
| 32 | C₂H₅Br | H | 3-methylpiperidine | N⁺(CH₃)(C₂H₅) | Br⁻ | 175–177 (AC) |
| 33 | C₂H₅Br | H | pyrrolidine | N⁺(CH₃)(C₂H₅) | Br⁻ | 156–160 (A—E) |
| 34 | C₂H₅I | H | piperidine | N⁺(CH₃)(C₂H₅) | I⁻ | 180–184 (AC—A—E) |
| 35 | C₂H₅Br | H | 4-methylpiperidine | N⁺(CH₃)(C₂H₅) | Br⁻ | 139–141 (AC—E) |
| 36 | CH₃Br | H | piperidine | N⁺(CH₃)₂ | Br⁻ | 217–219 (A) |
| 37 | CH₃Br | H | 4-methylpiperidine | N⁺(CH₃)₂ | Br⁻ | 200–203 (A—M) |

TABLE 5-continued

| Ex. | R₆X | R₁ | Am | T | | m.p. (°C.) (Recry. Solv.*) |
|---|---|---|---|---|---|---|
| 38 | $CH_3Br$ | H | -N (7-membered ring) | -piperidyl-N⁺(CH₃)₂ | Br⁻ | 204–207 (A—M) |
| 39 | $CH_3Br$ | H | -N (5-membered ring) | -piperidyl-N⁺(CH₃)₂ | Br⁻ | 180–182 (A) |
| 40 | $CH_3I$ | H | -N (7-membered ring with CH₃) | -piperidyl-N⁺(CH₃)₂ | I⁻ | 229–231 (AC) |
| 41 | $C_2H_5I$ | H | -N (7-membered ring) | -piperidyl-N⁺(C₂H₅)₂ | I⁻ | 142–145 (A) |
| 42 | $CH_3I$ | 5-Cl | -N (7-membered ring) | -piperidyl-N⁺(CH₃)₂ | I⁻ | 212–213 (AN) |
| 43 | $CH_3I$ | 6-F | -N (7-membered ring) | -piperidyl-N⁺(CH₃)₂ | I⁻ | 192–194 (A) |
| 44 | $CH_3I$ | 5-F | -N (7-membered ring) | -piperidyl-N⁺(CH₃)₂ | I⁻ | 192–196 (A) |

[Note]
*The abbreviations are as follows:
A: ethanol, AC: acetone, EA: ethyl acetate, AN: acetonitrile, E: diethyl ether, M: methanol.

The starting materials as used in Examples 1 to 16 were prepared in the following manner.

REFERENCE EXAMPLE 1

1-Methyl-4-piperidyl 1,2-benzisoxazole-3-acetate hydrobromide p-Toluenesulfonyl chloride (2.16 g) and 4-hydroxy-1-methylpiperidine (4 g) were added in turn to a solution of 1,2-benzisoxazole-3-acetic acid (2.0 g) in dry toluene (200 ml). The mixture was stirred overnight at room temperature and then shaken with 5% sodium carbonate (20 ml) and water (100 ml). The toluene layer was washed with water and dried over anhydrous sodium sulfate. The toluene was distilled off in vacuo and the residue was dissolved in diethyl ether. An ethanolic solution of 47% hydrobromic acid was added to the ether solution. The resulting crystals were collected by filtration and recrystallized from a mixture of ethanol and diethyl ether to give 1-methyl-4-piperidyl 2-(1,2-benzisoxazol-3-yl)acetate hydrobromide (2.8 g), m.p. 179°–181° C.

REFERENCE EXAMPLE 2

1-Methyl-3-piperidyl 1,2-benzisoxazole-3-acetate hydrobromide

3-Hydroxy-1-methylpiperidine (1.3 g) was added to a solution of 1,2-benzisoxazole-3-acetic acid (2.0 g) in dry dioxane (13 ml) and thereto was added dropwise phosphorus oxychloride (0.7 g). The reaction mixture was heated at 80°–90° C. for 23 hours and then evaporated to dryness in vacuo. To the residue was added water and the resulting mixture was made alkaline with aqueous ammonia solution and extracted with toluene. The toluene layer was washed with water, dried over anhydrous sodium sulfate and evaporated in vacuo. The residue was treated in substantially the same manner as in Reference Example 1 to give 1-methyl-3-piperidyl 1,2-benzisoxazole-3-acetate hydrobromide (2.7 g), m.p. 128°–129° C.

REFERENCE EXAMPLE 3

1-Methyl-4-piperidyl 2-(5-chloro-1,2-benzisoxazol-3-yl)acetate hydrobromide

A mixture of 5-chloro-1,2-benzisoxazole-3-acetic acid (1.05 g), p-toluenesulfonyl chloride (1 g), and dry toluene (100 ml) was refluxed for 1 hour and allowed to cool to room temperature. To the mixture was added 4-hydroxy-1-methylpiperidine (1.7 g). The resulting mixture was stirred for 1 day at room temperature and then shaken with 5% sodium carbonate (10 ml) and water (100 ml). The toluene layer was washed with water and extracted with 5% hydrochloric acid. The aqueous layer was made alkaline by addition of aqueous ammonia solution and extracted with toluene. The toluene layer was dried over anhydrous sodium sulfate and evaporated in vacuo. The residue was dissolved in ethanol and thereto was added an ethanolic hydrobromic acid. The resulting mixture was evaporated in vacuo and the residue was recrystallized from a mixture of ethanol and diethyl ether to give 1-methyl-4-piperidyl 2-(5-chloro-1,2-benzisoxazol-3-yl)acetate hydrobromide (1.0 g), m.p. 200°–201° C.

REFERENCE EXAMPLE 4

The following oily compounds were prepared in substantially the same manner as in Reference Examples 1 to 3, using the corresponding 1,2-benzisoxazole-3-acetic acids and hydroxypiperidines:

1-methyl-4-piperidyl 5-fluoro-1,2-benzisoxazole-3-acetate, 1-methyl-4-piperidyl 6-fluoro-1,2-benzisoxazole-3-acetate, 1-ethyl-3-piperidyl 1,2-benzisoxazole-3-acetate, and 1-ethyl-4-piperidyl 1,2-benzisoxazole-3-acetate.

REFERENCE EXAMPLE 5

1-Methyl-4-piperidyl 2-bromo-2-(1,2-benzisoxazol-3-yl)acetate hydrobromide

A solution of bromine (1.12 g) in glacial acetic acid (2 ml) was added dropwise at 60° C. with stirring to a solution of 1-methyl-4-piperidyl 1,2-benzisoxazole-3-acetate hydrobromide (2.0 g) in glacial acetic acid (8 ml). The reaction mixture was stirred for 3 hours at 60° C. and then concentrated in vacuo to about a half volume. The residue was dissolved in acetone and thereto was added diethyl ether until it became turbid. After cooling, the resulting crystals were collected by filtration to give 1-methyl-4-piperidyl 2-bromo-2-(1,2-benzisoxazol-3-yl)acetate hydrobromide (1.9 g). An analytical sample was obtained by recrystallization from ethanol, m.p. 169°–171° C.

EXAMPLE 45

|  | per 1,000 tablets |
|---|---|
| 1-Ethyl-1-methyl-4-[2-hexamethyleneimino-2-(1,2-benzisoxazol-3-yl)-acetoxy]piperidinium iodide | 20 g |
| Corn starch | 28 g |
| Lactose | 65 g |
| Microcrystalline cellulose | 30 g |
| Hydroxypropylcellulose | 5 g |
| Light anhydrous silicic acid | 1 g |
| Magnesium stearate | 1 g |

The above components were blended, granulated and made into tablets by a conventional method to form 1,000 tablets, each weighing 150 mg.

EXAMPLE 46

|  | per 1,000 capsules |
|---|---|
| 1-Ethyl-1-methyl-4-[2-hexamethyleneimino-2-(1,2-benzisoxazol-3-yl)-acetoxy]piperidinium iodide | 40 g |
| Corn starch | 80 g |
| Lactose | 56 g |
| Microcrystalline cellulose | 40 g |
| Talc | 2 g |
| Magnesium stearate | 2 g |

The above components were blended, granulated and filled into 1,000 capsules by a conventional method.

EXAMPLE 47

|  |  |
|---|---|
| 1-Ethyl-1-methyl-4-[2-hexamethyleneimino-2-(1,2-benzisoxazol-3-yl)-acetoxy]piperidinium iodide | 100 g |
| Corn starch | 200 g |
| Lactose | 660 g |
| Light anhydrous silicic acid | 10 g |
| Hydroxypropylcellulose | 30 g |

The above components were blended and made into fine granules by a conventional method.

What is claimed is:

1. A tertiary amine compound of the formula:

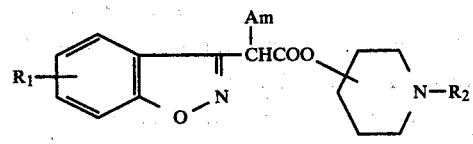

wherein $R_1$ is hydrogen or halogen atom, $R_2$ is a lower alkyl group, Am is a 5- to 9-membered saturated cyclic amino group which may be substituted by a lower alkyl group, and the group:

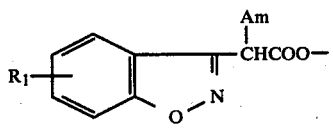

binds to the piperidine moiety at 3- or 4-position of the latter, or a pharmaceutically acceptable acid addition salt thereof.

2. A compound or a pharmaceutically acceptable acid addition salt thereof according to claim 1, wherein $R_1$ is hydrogen or 5- or 6-halogen atom, $R_2$ is methyl or ethyl group, and Am is a 5- to 8-membered saturated cyclic amino group which may be substituted by methyl group.

3. A compound or a pharmaceutically acceptable acid addition salt thereof according to claim 2, wherein $R_1$ is hydrogen atom, and Am is hexamethyleneimino group.

4. A compound according to claim 3, which is 1-methyl-4-piperidyl 2-hexamethyleneimino-2-(1,2-benzisoxazol-3-yl)acetate or a pharmaceutically acceptable acid addition salt thereof.

5. A quaternary ammonium salt of the formula:

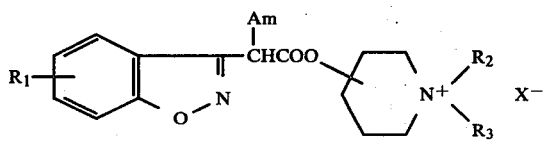

wherein R₁ is hydrogen or a halogen atom, R₂ is a lower alkyl group, R₃ is an alkyl group or a phenylalkyl group which may be substituted by a lower alkoxy or methylenedioxy group, Am is a 5- to 9-membered saturated cyclic amino group which may be substituted by a lower alkyl group, X⁻ is a pharmaceutically acceptable anion, and the group:

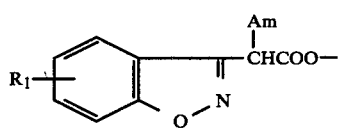

binds to the piperidine moiety at 3- or 4-position of the latter.

6. A quaternary ammonium salt according to claim 5, wherein X⁻ is an anion selected from the group consisting of a halide ion, a lower alkylsulfate ion, a lower alkyl sulfonate ion, a substituted or unsubstituted benzenesulfonate ion, and nitrate ion.

7. A quaternary ammonium salt according to claim 5, wherein X⁻ is bromide or iodide ion.

8. A quaternary ammonium salt according to claim 5, 6 or 7, wherein R₁ is hydrogen or 5- or 6-halogen atom, R₂ is methyl or ethyl group, and Am is a 5- to 8-membered saturated cyclic amino group which may be substituted by methyl group.

9. A quaternary ammonium salt according to claim 8, wherein R₁ is hydrogen atom and Am is hexamethyleneimino group.

10. A quaternary ammonium salt according to claim 5, 6 or 7, wherein R₁ is hydrogen or 5- or 6-halogen atom, Am is a 5- to 8-membered saturated cyclic amino group which may be substituted by methyl group, and R₂ and R₃ are both methyl group, or either one of R₂ and R₃ is methyl group and another one of them is ethyl group.

11. A quaternary ammonium salt of the formula:

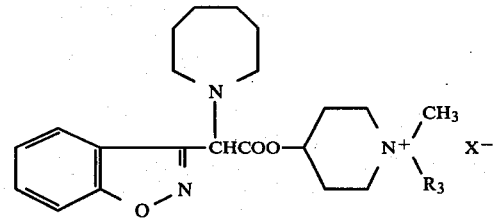

wherein R₃ is methyl or ethyl group, and X⁻ is a pharmaceutically acceptable anion.

12. A quaternary ammonium salt according to claim 11, wherein X⁻ is an anion selected from the group consisting of a halide ion, a lower alkylsulfate ion, a lower alkylsulfonate ion, a substituted or unsubstituted benzenesulfonate ion and nitrate ion.

13. 1-Ethyl-1-methyl-4-[2-hexamethyleneimino-2-(1,2-benzisoxazol-3-yl)acetoxy]piperidinium iodide.

14. 1-Ethyl-1-methyl-4-[2-hexamethyleneimino-2-(1,2-benzisoxazol-3-yl)acetoxy]piperidinium bromide.

15. 1,1-Dimethyl-4-[2-hexamethyleneimino-2-(1,2-benzisoxazol-3-yl)acetoxy]piperidinium iodide.

16. 1,1-Dimethyl-4-[2-hexamethyleneimino-2-(1,2-benzisoxazol-3-yl)acetoxy]piperidinium bromide.

17. A pharmaceutical composition comprising an antispasmodic effective amount of a tertiary amine compound as set forth in claim 1, or a pharmaceutically acceptable acid addition salt thereof and a pharmaceutically acceptable carrier.

18. A pharmaceutical composition comprising an antispasmodic effective amount of a quaternary ammonium salt as set forth in claim 5 and a pharmaceutically acceptable carrier.

19. A pharmaceutical composition comprising an antispasmodic effective amount of a quaternary ammonium salt as set forth in claim 10 and a pharmaceutically acceptable carrier.

20. A pharmaceutical composition comprising an antispasmodic effective amount of a quaternary ammonium salt as set forth in claim 11 and a pharmaceutically acceptable carrier.

21. A pharmaceutical composition comprising an antispasmodic effective amount of a quaternary ammonium salt as set forth in claim 13 and a pharmaceutically acceptable carrier.

22. A pharmaceutical composition comprising an antispasmodic effective amount of a quaternary ammonium salt as set forth in claim 14 and a pharmaceutically acceptable carrier.

23. A pharmaceutical composition comprising an antispasmodic effective amount of a quaternary ammonium salt as set forth in claim 15 and a pharmaceutically acceptable carrier.

24. A pharmaceutical composition comprising an antispasmodic effective amount of a quaternary ammonium salt as set forth in claim 16 and a pharmaceutically acceptable carrier.

* * * * *